(12) United States Patent
Shiffman et al.

(10) Patent No.: US 7,415,447 B2
(45) Date of Patent: *Aug. 19, 2008

(54) APPARATUS AND METHOD FOR PREDICTION AND MANAGEMENT OF PARTICIPANT COMPLIANCE IN CLINICAL RESEARCH

(75) Inventors: Saul Shiffman, Pittsburgh, PA (US); Michael R. Hufford, San Diego, CA (US); Jean A. Paty, Pittsburgh, PA (US)

(73) Assignee: Invivodata, Inc., Scotts Valley, CA (US)

( * ) Notice: Subject to any disclaimer, the term of this patent is extended or adjusted under 35 U.S.C. 154(b) by 158 days.

This patent is subject to a terminal disclaimer.

(21) Appl. No.: 11/324,504

(22) Filed: Jan. 3, 2006

(65) Prior Publication Data

US 2006/0184493 A1    Aug. 17, 2006

Related U.S. Application Data

(63) Continuation-in-part of application No. 11/002,046, filed on Dec. 1, 2004, which is a continuation of application No. 09/825,534, filed on Apr. 2, 2001, now Pat. No. 6,879,970.

(51) Int. Cl.
  *G06F 17/00* (2006.01)
  *G06N 5/00* (2006.01)
  *G06N 5/02* (2006.01)

(52) U.S. Cl. .................. 706/47; 706/45; 706/46

(58) Field of Classification Search ............. None
See application file for complete search history.

(56) References Cited

U.S. PATENT DOCUMENTS 4,918,627 A * 4/1990 Garcia et al. ............ 702/82
5,307,262 A * 4/1994 Ertel .......................... 705/2
5,479,339 A * 12/1995 Miller ....................... 700/16

(Continued)

OTHER PUBLICATIONS 3B-1 Noninvasive Insulin Delivery in Large Pigs (> 100lbs) Using the Lightweight Cymbal Array Eun-Joo Park; Werner, J.; Smith, N.B.; Ultrasonics Symposium, 2007. IEEE Oct. 28-31, 2007 pp.: 104-107 Digital Object Identifier 10.1109/ULTSYM.2007.39.*

(Continued)

*Primary Examiner*—Michael B Holmes
(74) *Attorney, Agent, or Firm*—Lahive & Cockfield, LLP; Kevin J. Canning

(57) ABSTRACT

A system for developing and implementing empirically derived algorithms to generate decision rules to determine participant noncompliance and fraud with research protocols in clinical trials allows for the identification of complex patterns of variables that detect or predict participant noncompliance and fraud with research protocol, including performance and enrollment goals, in the clinical trial. The data may be used to overall predict the performance of any participant in a clinical trial, allowing selection of participants that tend to produce useful, high-quality results. The present invention can also be used to monitor participant compliance with the research protocol and goals to determine preferred actions to be performed. Optionally, the invention may provide a spectrum of noncompliance, from minor noncompliance needing only corrective feedback, to significant noncompliance requiring participant removal from the clinical trial or from future clinical trials. The algorithms and decision rules can also be domain-specific, such as detecting non-compliance or fraud among subjects in a cardiovascular drug trial, or demographically specific, such as taking into account gender, age or location, which provides for algorithms and decision rules to be optimized for the specific sample of participants being studied.

30 Claims, 2 Drawing Sheets

U.S. PATENT DOCUMENTS

| | | | | |
|---|---|---|---|---|
| 5,547,878 | A * | 8/1996 | Kell | 436/111 |
| 5,596,994 | A * | 1/1997 | Bro | 600/545 |
| 5,652,146 | A * | 7/1997 | Kell | 436/111 |
| 5,908,788 | A * | 6/1999 | Kell | 436/111 |
| 6,029,144 | A * | 2/2000 | Barrett et al. | 705/30 |
| 6,165,142 | A * | 12/2000 | Bar | 600/595 |
| 6,338,039 | B1 * | 1/2002 | Lonski et al. | 705/3 |
| 6,879,970 | B2 * | 4/2005 | Shiffman et al. | 706/21 |
| 7,054,782 | B2 * | 5/2006 | Hartlaub | 702/138 |
| 7,072,802 | B2 * | 7/2006 | Hartlaub | 702/188 |
| 7,124,059 | B2 * | 10/2006 | Wetzer et al. | 702/184 |
| 7,249,043 | B1 * | 7/2007 | Trout, II et al. | 705/8 |
| 7,251,620 | B2 * | 7/2007 | Walker et al. | 705/26 |
| 7,343,337 | B1 * | 3/2008 | Cieliebak et al. | 705/36 R |

OTHER PUBLICATIONS

A Smart and Passive Floor-Vibration Based Fall Detector for Elderly Alwan, M.; Rajendran, P.J.; Kell, S.; mack, D.; Dalal, S.; Wolfe, M.; Felder, R.; Information and Communication Technologies, 2006. ICTTA '06. 2nd vol. 1, Apr. 24-28, 2006 pp.: 1003-1007.*

Incremental adoption of information security in health-care organizations: implications for document management Lorence, D.P.; Churchill, R.; Information Technology in Biomedicine, IEEE Transactions on vol. 9, Issue 2, Jun. 2005 pp.: 169-173 Digital Object Identifier 10.1109/TITB.2005.847137.*

Towards an expert system for treatment planning Shalev, S.; Viggars, D.; Hahn, P.; Stewart, M.; Engineering in Medicine and Biology Society, 1988. Proceedings of the Annual International Conference of the IEEE Nov. 4-7, 1988 pp.: 1444-1445 vol. 3 Digital Object Identifier 10.1109/IEMBS.1988.95302.*

* cited by examiner

APPARATUS AND METHOD FOR PREDICTION AND MANAGEMENT OF PARTICIPANT COMPLIANCE IN CLINICAL RESEARCH

REFERENCE TO RELATED APPLICATIONS

This application is a continuation-in-part of U.S. patent Ser. No. 11/002,046, which is a continuation of application Ser. No. 09/825,534 filed Apr. 2, 2001, now U.S. Pat. No. 6,879,970 issued Apr. 12, 2005. The subject matter of this application relates to the patent application titled "System for Clinical Trial Subject Compliance", application Ser. No. 09/825,533, filed Apr. 2, 2001. The aforementioned application, and the references cited therein, are incorporated herein by reference.

FIELD OF THE INVENTION

The present invention relates to predicting the behavior of a clinical trial participant during research, especially clinical trials. Specifically, the invention relates to the prediction of clinical trial participant compliance with protocols, including performance and enrollment goals, in clinical trials.

BACKGROUND OF THE INVENTION

Evaluation of the compliance of a clinical trial participant with research protocols, including research goals, typically looks at only one variable at a time. Such evaluation is not empirically derived by quantitative analysis of existing datasets, instead relying on the researcher's or sponsors' judgment and biases to determine whether and what type of corrective action is required. Furthermore, evaluation of compliance of a clinical trial participant with clinical trial protocols has typically not taken into account the domain of the clinical trial or the characteristics of the participants. Finally, such evaluation often cannot be made in a timely way, but is made only after serious noncompliance has already occurred.

Each year, many resources, including money and time, are wasted on clinical trial sites that fail to comply with research protocols, including failure to produce any data, a sufficient amount of data or reliable data. For example, many clinical trial sites provide inaccurate data due to poor training or non-compliance with research protocol. Resources may be devoted to clinical trial sites that fail to enroll a sufficient number of subjects, or even one subject, producing little useful data in view of the amount of resources devoted to setting up the clinical trial. Further, participants in the clinical, such as subjects, trial investigators, research coordinators, site staff, and study monitors, may on occasion falsify data for the trial, possibly resulting in erroneous conclusions and creating liability for the trial's sponsor. Therefore, identification of clinical trial sites or other clinical trial participants that tend to produce results that are adequate in quantity and quality, and those that do not produce adequate results may provide enormous conservation of resources.

SUMMARY OF THE INVENTION

The present invention provides a system and method for determining participant compliance in a clinical trial based on quantitative analysis of historical compliance data obtained by or about the participant. Compliance may relate to adherence to set procedures, achievement of certain goals of a clinical trial, or any other parameter indicative of performance. The historical compliance data may be obtained at any point previous to the quantitative analysis, such as at an earlier clinical trial, or at an earlier point in a clinical trial for which compliance is determined. The determination of compliance may predict future compliance or noncompliance, or identify past instances of compliance or noncompliance.

The goal of clinical trials is to collect valid, reliable data on one or more conditions within a clinical trial group of subjects. Subjects in clinical trials are assigned tasks related to treatment and data collection in accordance with a research protocol. The integrity of clinical trials rests upon subjects' faithful performance of these tasks, as well as the compliance of other clinical trial participants, such as doctors, nurses, the overall site and so on, with clinical trial protocol and its requirements. Compliance with clinical trial protocol is generally indicative of overall performance. If clinical trial participants fail to comply with the protocol, the trial fails to yield reliable, valid results. Thus, participant noncompliance in clinical trials is a significant risk and cost to the pharmaceutical industry. Accordingly, predicting participant performance, quality of data collected during a clinical trial, and assessment of such performance is of substantial value to clinical research.

The benefits of a system that can predict and track compliance of a participant in a clinical trial include: reliable, valid data; increased statistical power; reduced clinical trial costs through smaller sample sizes; reduced time to complete the clinical trial; conservation of resources by avoiding non-producing clinical trial participants, reduced noise in the data that would be introduced by poorly-performing investigators, research coordinators, and sites and, ultimately, reduced time to get a drug or medical device to market. The system may, for example, identify clinical trial sites that tend to do a poor job, such as those that provide less reliable or accurate data, provide poor training to subjects, produce few, if any, evaluative subjects, or produce little or no data, allowing sponsors or researchers to avoid using such sites for conducting a clinical trial.

According to one embodiment of the invention, a method of predicting noncompliance in a clinical trial participant is provided. The method includes the steps of providing historical compliance data for a clinical trial participant, and generating at least one predictive algorithm for predicting noncompliance of the clinical trial participant by quantitative analysis of the historical compliance data.

The at least one predictive algorithm may be translated into at least one prediction rule for use within either the on-going clinical trial, or for future application in other clinical trials.

In another embodiment of the invention, a method of identifying a suitable clinical trial site for conducting a clinical trial is provided, comprising the steps of providing a database storing historical compliance data for a plurality of clinical trial sites, performing a statistical analysis of the historical compliance data for each clinical trial site to predict compliance in a future clinical trial and selecting a clinical trial site that is predicted to comply with research protocols.

In another embodiment of the invention, a method of predicting success of a clinical trial involving a selected clinical trial participant is a provided. The method of predicting success comprises the steps of providing historical compliance data from a clinical trial involving the clinical trial participant and performing a quantitative analysis of the data to identify whether the participant is likely to produce data in compliance with research protocol in the future.

According to another embodiment, a method of determining noncompliance of a clinical trial participant includes the steps of providing at least one of the group of historical participant compliance data and historical protocol data and generating at least one algorithm reflective of at least one of historical participant compliance data and historical protocol data by quantitatively analyzing the historical participant compliance data and the historical protocol data. The method also includes translating the algorithm into at least one decision rule for analyzing participant compliance information, obtaining the participant compliance information and comparing the participant compliance information to the at least one decision rule to determine if corrective action is needed.

According to a further embodiment, a method of the invention includes the steps of providing historical participant compliance data and historical protocol data, generating a spectrum of noncompliance representative of the historical participant compliance data not compliant with the historical protocol data by quantitative analysis of the historical participant compliance data and the historical protocol data, obtaining participant compliance information and comparing the spectrum of noncompliance to the participant compliance information to determine if corrective action is needed.

According to an embodiment of the invention a method of detecting fraud by a participant in a clinical trial is provided, having the steps of providing historical participant compliance data and historical protocol data, generating at least one fraud detection algorithm for detecting participant fraud by quantitative analysis of the historical participant compliance data and the historical protocol data and translating the at least one fraud detection algorithm into at least one fraud detection rule for use with a clinical trial.

According to an embodiment of the invention another method of detecting fraud by a participant in a clinical trial is provided, having the steps of providing participant compliance data, generating at least one fraud detection algorithm for detecting subject fraud by quantitative analysis of the compliance data and translating the at least one fraud detection algorithm into at least one fraud detection rule for use with a clinical trial.

According to an embodiment of the invention a medium suitable for use in an electronic device and having instructions for execution on the electronic device, the instructions, having the steps of providing at least one of the group of historical participant compliance data and historical protocol data, generating at least one predictive algorithm for predicting participant noncompliance by quantitative analysis of at least one of the group of the historical participant compliance data and the historical protocol data and translating the at least one predictive algorithm into at least one prediction rule for use with a clinical trial.

According to another embodiment of the invention a medium suitable for use in an electronic device and having instructions for execution on the electronic device, the instructions having the steps of providing at least one of the group of historical participant compliance data and historical protocol data, generating at least one algorithm reflective of at least one of the group of the historical participant compliance data and the historical protocol data by quantitative analysis of the historical participant compliance data and the historical protocol data, translating the at least one algorithm into at least one decision rule for analyzing participant compliance information, obtaining the participant compliance information and comparing the participant compliance information to the at least one decision rule to determine if corrective action is needed.

According to another embodiment of the invention a medium suitable for use in an electronic device and having instructions for execution on the electronic device, the instructions having the steps of providing historical participant compliance data and historical protocol data, generating a spectrum of noncompliance representative of the historical participant compliance data not compliant with the historical protocol data by quantitative analysis of the historical participant compliance data and the historical protocol data, obtaining participant compliance information and comparing the spectrum of noncompliance to the participant compliance information to determine if corrective action is needed.

According to a further embodiment of the invention a medium suitable for use in an electronic device and having instructions for execution on the electronic device, the instructions having the steps of providing historical participant compliance data and historical protocol data, generating at least one fraud detection algorithm for detecting participant fraud by quantitative analysis of the historical participant compliance data and the historical protocol data and translating the at least one fraud detection algorithm into at least one fraud detection rule for use with a clinical trial.

According to an embodiment of the invention a medium suitable for use in an electronic device and having instructions for execution on the electronic device, the instructions having the steps of providing participant compliance data, generating at least one fraud detection algorithm for detecting participant fraud by quantitative analysis of the compliance data and translating the at least one fraud detection algorithm into at least one fraud detection rule for use with a clinical trial.

BRIEF DESCRIPTION OF THE DRAWINGS

The foregoing and other objects, features and advantages of the invention will be apparent from the following description and apparent from the accompanying drawings.

DETAILED DESCRIPTION OF THE INVENTION

Figure 1:
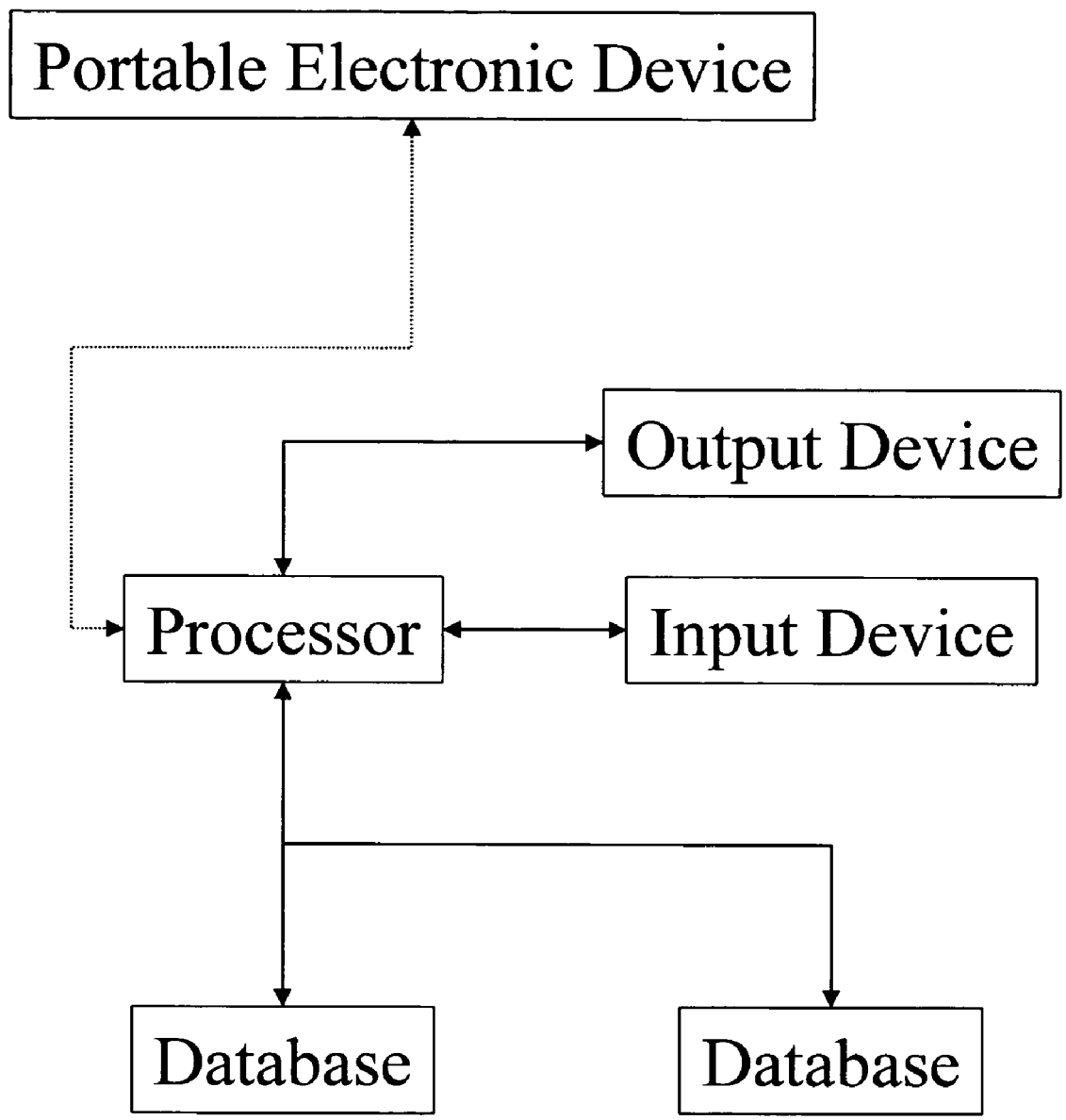
FIG. 1 illustrates a system for determining noncompliance of a participant in a clinical trial according to the teachings of the present invention.

The present invention involves an empirically derived set of algorithms and decision rules to identify and/or predict compliance of a participant in a clinical trial, and detect noncompliance, with research protocols, which may include performance and enrollment goals. The present invention uses algorithms and decision rules to provide an empirical approach for predicting different types of participant noncompliance with research protocols. This actuarial approach to determining participant noncompliance with clinical trial protocols is consistent with empirical research demonstrating the superiority of actuarial prediction of human behavior as compared to subjective clinical judgment. According to an alternative embodiment of the invention, a portable electronic device is used to query and collect data from one or more clinical trial participants to determine compliance and/or noncompliance. For example, the present invention may be used to record, assess and/or predict how well a given clinical trial site or other participant does at adhering to clinical trial protocols or achieving the goals of the clinical trial, for example, achieving enrollment targets. As another example, the present invention could be used to record or predict how well a subject in a clinical trial has adhered to or will adhere to the requirements of the clinical trial.

As used herein "clinical trial" refers to a broad range of data collecting activities, including studies directed to monitoring of one or more conditions within a clinical trial group of subjects. One such example includes drug trials involving humans.

As used herein, "protocol" or "clinical trial protocol" refers to plan for a clinical trial, including set procedures for performing the clinical trial, and performance goals, such as enrollment targets, for the clinical trial.

As used herein "compliance" refers to a parameter indicative of the quality and/or performance of a participant in a clinical trial, generally indicated by adherence to protocol, such as adherence to set procedures in a clinical trial, adherence to or achievement of certain goals of a clinical trial, such as enrollment goals, and/or any other parameter indicative of overall performance of a participant in a clinical trial.

As used herein "clinical trial participant" or "participant" refer to any person, place or thing involved in a clinical trial, including, but not limited to, doctors, nurses and other medical professionals, administrators of a clinical trial, investigators, study coordinators, data and site monitors, data collectors, subjects in a clinical trial, clinical trial monitors, as well as the overall clinical trial site, sponsoring pharmaceutical company and contract research organizations that provide training for clinical trial sites and personnel. Participants may collect data from a clinical trial, provide data during a clinical trial, record data during a clinical trial, administer instructions to other participants in a clinical trial, enroll subjects to participate in a clinical trial, and/or perform any other task associated with the procedures of a clinical trial. Clinical trial monitors are generally personnel, such as from a sponsoring pharmaceutical company, or of a third-party contract research organization, which monitor the activities of the research sites, including the activities of other clinical trial participants.

As used herein "subject" refers to any participant in a clinical trial about whom clinical data is collected, whether or not the subject has any relationship to a doctor or other health care provider.

"Trial data" or "clinical trial data" refers to data gathered for the principle purpose of the clinical trial. For example, trial data would include pain levels experienced by subjects in a pain medication clinical trial or craving levels in an anti-smoking medication clinical trial.

"Evaluability data" or "compliance data" or "compliance information" is data indicative of performance and/or compliance of a participant with clinical trial goals and procedures (i.e., protocol). Historical compliance data is any data collected at any point in time prior to analysis, and may be collected during an earlier clinical trial, or earlier in the same clinical trial for which an analysis of the compliance data is conducted. Compliance data may relate to the circumstances under which the trial data was collected or other data pertaining to characteristics, including the quality, of the trial data or other evaluability data. Some examples include overall performance, timeliness, consistency with other collected data, data quality (e.g., number of checks and edits, audit reports and so on), proximity of the data to an expected data range, completeness of the data, enrollment numbers in the clinical trial, enrollment targets and achievement of enrollment targets, previous compliance information for a particular site, such as historical tendency of a site to reach targeted enrollment goals, produce useful, compliant data, consistency of instructions or training given to participants with model instructions or training, and monitoring provided during the performance of a clinical trial.

"Historical protocol data" includes data specifying the research protocol of earlier clinical trials or from earlier within the same clinical trial. Historical protocol data is not limited to data from an entirely different trial, but also includes an application to an interim analysis to an on-going trial (e.g., long-term safety trial). As used herein, research protocol may include research goals, such as a target enrollment level in a clinical trial. Examples of historical protocol data can include questions posed to subjects, frequency of prompting of a subject during various times of the day or week, time allowed for subjects to respond to questions, requirements of subject behavior, conditions mandating removal of a subject from certain statistical analyses or removal as participant in the clinical trial, demands or expectations imposed upon the sites, targets for subject enrollments, and so on.

As used herein "portable electronic device" refers to any electronic device that can be adapted for use by a subject and/or clinical staff for viewing and/or inputting information. Preferably, the portable electronic device will also have a visual, audible or tactile alarm to gain the attention of the subject. For example, a pager having a vibration alarm may be used as a portable electronic device. Further examples include pagers with audible alarms and/or text messaging capabilities, a laptop computer or a cell phone. Preferably, according to the invention, a portable electronic device will be a handheld computer provided with a display and a data input feature, such as a touch-sensitive screen, or buttons to enable a subject to respond to questions posed on the display or to input unsolicited information. Examples of such portable electronic devices include the Palm Pilot by Palm, Inc or Windows-based devices running Pocket PC from Microsoft Corporation. Preferably, the portable electronic device will also be adapted to communicate with at least one other computer via a wireless connection or via a wired connection, including the use of a modem and/or a network, such as a LAN or the Internet.

According to an embodiment of the present invention, a system is provided as shown in FIG. 1. A processor 10 is provided and is adapted to communicate with at least one database 20. As discussed below, the database preferably stores data related to participant compliance and associated research protocols. An input device 30 is also provided to allow the subject or another person to provide input to the processor 10. The input device 30 may be a keyboard, a modem or other such device adapted for communication with the processor. An output device 40 is also preferably provided to receive and display information from the processor 10. Examples of output devices 40 include a printer and a monitor.

In one embodiment of the invention, a portable electronic device 50 is provided and is selectively operatively coupled to the processor 10. The portable electronic device 50 can also include a processor and may serve as an alarm, an input device, an output device, and/or a database. One example of a portable electronic device is a Palm Pilot by Palm, Inc, as described above. However, a portable electronic device is not a necessary component of the invention.

Figure 2:
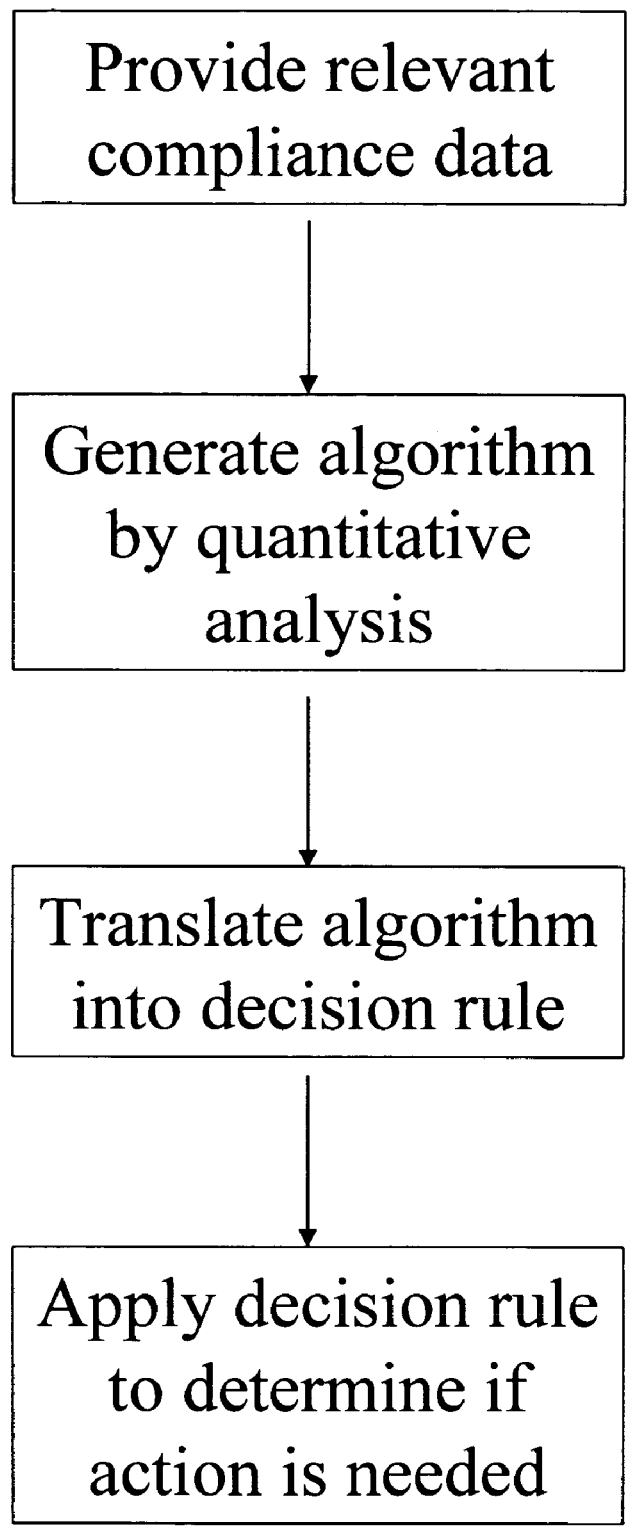
FIG. 2 is a schematic flow chart diagram illustrating the method according to the teachings of the present invention.

According to an embodiment of the invention, a flow chart illustrating the method of the present invention is set forth in FIG. 2. First, relevant participant compliance data, and associated protocol data, reflecting participant compliance with research protocols in clinical trials, is provided, step 110. The compliance data may be from an earlier clinical trial, or be taken at an earlier point in time during the same clinical trial for which the analysis is performed. Optionally, only participant compliance data may be provided, as some application of the present invention may not require knowledge of associated historical protocol for use of the participant compliance data. For example, analysis of response times to questions may not require knowledge of the maximum permissible time for subjects to answer questions in earlier clinical trials or analysis of enrollment numbers may not require knowledge of previous enrollment targets.

Participant compliance data and associated protocol data is preferably stored in one or more databases 20 and may be identified from earlier clinical trials and/or earlier activities of a current clinical trial. An output of the present invention preferably includes a database to provide participant compliance data and associated protocol data for later use by the invention.

For compliance data regarding a subject in a clinical trial, the compliance data and associated protocol data is preferably specific to the type of condition or medication that is the focus of the clinical trial. For example, if the clinical trial relates to a cardiovascular condition, the data preferably relates to subject compliance with protocols in cardiovascular clinical trials. Likewise, if the clinical trial relates to a cardiovascular medication, the data used in the present invention will preferably relate to subject compliance with protocols in cardiovascular clinical trials. It is also within the scope of the invention to optionally include subject compliance data and associated protocol data obtained from an earlier phase of the clinical trial into the compliance data of the present invention. Alternatively, the subject compliance data and associated protocol data may not be related to the type of condition or medication that is the focus of the clinical trial.

For overall compliance data regarding a particular clinical trial site as a participant, the compliance data and associated protocol data may be specific to the clinical trial site's ability to produce usable, compliant data. For example, to identify sites that traditionally enroll large numbers of participants, the compliance data provided and used in step 110 may relate to enrollment levels and/or the historic ability of the particular clinical trial site to reach enrollment targets. To identify sites that tend to produce the most accurate data, the compliance data provided and used in step 110 may relate to how compliant these sites were in previous clinical trials or earlier in the same clinical trial with respect to training, subject compliance, and regular trial monitoring. In addition, the compliance with instructions and research protocol of individual subjects participating in a clinical trial at a clinical trial site may be used to evaluate the quality of that particular clinical trial site. The historical data on site or personnel compliance may be specific to that site or person, or may relate to historical performance of a class of sites (e.g., contract research organization sites, independent sites, small sites, large sites, sites grouped by geographic regions, and so on) or persons (e.g., particular medical specialties, seniority and experience in clinical trials, tenure at the site, or other factors).

For compliance data for a monitor of a clinical trial, the compliance data may relate to how well the monitor complied with the monitoring procedures of the clinical trial.

For compliance data for an administrator of a clinical trial, the compliance data may relate to whether the instructions given to a subject regarding the collection of data were consistent with model instructions.

For compliance data relating to a contract research organization, the compliance data may related to the quality of the training for the clinical trial sites and personnel provided by the contract research organization.

The compliance data obtained in step 110 may be any parameter indicative of the performance of a particular participant in a clinical trial and are not limited to the above-described examples.

Next, at least one algorithm representative of the participant compliance data is generated by quantitative analysis of the compliance data, step 120. Preferably, multiple algorithms are generated. The present invention involves the application of statistical and other quantitative methods to screen existing research data for markers of, e.g. variables related to, noncompliance with research protocols, including research goals. Preferably, the participant compliance data is also reviewed to exclude invalid data. For example, data reported by one subject that appears to be well outside a range established by all other subjects can indicate invalid data.

Examples of various types of data that may be collected according to an embodiment of the invention to determine the quality of a participant by determining the compliance of the participant with clinical trial protocol may also include variables that may represent 'non-intuitive' predictors such as: gender of the subject or other participant about whom data is collected, disease severity, the time of the year, and the day of the week, location of the clinical trial site, demographic profile of the community surrounding a clinical trial site, experience and/or education level of the personnel participating in the clinical trial, salary level of employees of the clinical trial site, character of the clinical trial site (i.e., public university, private university, private doctor's office, research center, corporation whether the clinical trial site and/or participants have run any research in the past, how many clinical trials over what period of time, whether the investigator is an SAB member of the sponsor, and so on), number of employees involved in running a particular clinical trial or other data useful for predicting compliance and, therefore, overall performance. Additional prediction factors may also include characteristics of the research protocol, such as the nature of the subjects being recruited, the number of patients being recruited, the duration of the study, and may also include contractual aspects of the study, such as incentives for enrollment, payment per completed subject, and so on.

Quantitative analysis methods are used to distinguish, identify, and predict instances of good and poor compliance and/or instances of valid or invalid data. The quantitative analysis methods of the present invention may include, but are not limited to, application of a variety of statistical and data mining techniques, such as logistic regression, discriminant function analysis, classification and regression trees, neural networks, and multiple linear regression to screen existing data and derive algorithms to identify markers of noncompliance with research protocols.

Logistic regression analyses use dichotomous and continuous variables to predict dichotomous outcome variables. For example, dichotomous outcome variables can indicate "completed" or "failed to complete" a clinical trial monitoring protocol. Discriminant function analysis relates a categorical criterion variable to dichotomous or linear predictors. Classification and Regression Trees (CART) use binary recursive partitioning to identify unique groups of participants, such as, for example, subjects failing to complete the clinical trial protocol and subjects completing the protocol with minimal corrective feedback regarding their compliance with the clinical trial protocol, or sites that met recruitment targets versus those that did not. Neural network approaches to pattern recognition examine data for patterns and classify certain patterns of data based on the probability that they lead to a given outcome. Multivariate Regressive Splines (MARS) build flexible regression models, including interactions, by fitting separate splines to distinct intervals of the predictor variables.

Other nonparametric and parametric statistical approaches can also be applied to the prediction of participant noncompliance with clinical trial protocols, including clinical trial goals.

A variety of predictor and criterion variables can be used in the present invention. For subject compliance, predictor variables can range between basic demographic characteristics, such as, for example, gender of a subject or location of a clinical trial site, to specific clinical trial compliance related variables, such as, for example, mean latency to respond to an audible prompt from an optional portable electronic device or enrollment levels at a clinical trial site. Similarly, criterion variables can range from subtle, such as, for example, missing some percentage of portable electronic device prompts or failing to provide sufficient instructions to a subject, to severe noncompliance, such as, for example, failure to complete the clinical trial protocol or failure to enroll a single subject for a clinical trial. For detection of fraudulent entries, example predictor variables could include the speed or rate of entries, or an implausible or statistically unlikely pattern of answers to a set of assessment questions.

The present invention allows for complex, non-intuitive interactions among multiple variables to optimally predict participant compliance with clinical trial protocols, including clinical trial goals. That is, the markers or variables used to predict noncompliance may or may not, in and of themselves, be related to noncompliance. Algorithms may rely on different variables for different subgroups. For example, subgroups can include, but are not limited to, men and women, older or younger subjects, subjects late or early in the clinical trial, clinical trial sites associated with universities and clinical trial sites associated with corporations, clinical trial sites in cities and clinical trial sites in rural areas, clinical trial sites that provide extensive training and clinical trial sites that provide minimal training, clinical trial sites run by doctors and clinical trial sites run by other medical professionals, large studies or small studies, studies with enrollment targets and/or incentives versus those without such, and so on. The algorithms may also identify different combinations of variables working only in tandem. Thus, the variables alone may not be directly, simply, or obviously related to noncompliance. The algorithms of the invention may use complex and nonintuitive combinations of predictors to predict subject noncompliance with clinical trial protocols. The invention also allows context-specific algorithms to maximize predictive utility. That is, different algorithms can be derived for different groups of subjects, such as, for example, subjects with cardiovascular or central nervous system diseases, or from different kinds of sites, such as those that are part of a Contract Research Organization versus those that are not. As a result, the present invention avoids assuming that any given set of variables will be equally predictive of clinical trial noncompliance for all types of conditions or diseases or for all types of participants.

According to an embodiment of the invention, the present invention also provides for novel quantitative analyses to be incorporated into the development of algorithms to further improve their predictive validity. Specifically, the algorithms can be subject to continuous improvement as more data become available for analysis, either within an individual clinical trial or accumulating across clinical trials.

According to a further embodiment of the invention, algorithms can be used to determine appropriate feedback to subjects, research staff, sites, and sponsors regarding compliance with the protocol. For example, a computer program can implement decision rules based on these algorithms, and automatically determine appropriate feedback or action by the personnel involved in conducting or overseeing the clinical trial.

An advantage of the present invention is that, because the algorithms and decisions are based on formal, empirical, and quantitative criteria, they remove the subjective element in these decisions, which in turn minimizes the potential for bias. Another advantage is that the statistical algorithms can sometimes identify relationships that would not be evident to ordinary observation and/or relationships based on unintuitive variables or combinations of variables.

The above and other advantages provided by the disclosed invention include provisions for the application of these algorithms within existing and yet to be developed processes for giving systematic feedback to subjects, research sites, and clinical trial sponsors conducting clinical trials using clinical trials.

Once the one or more algorithms of the invention have been derived from analysis of existing data, the algorithms can be translated into specific decision rules, step 130. Decision rules are essentially reformatted algorithms that can be applied to current participant compliance data to determine whether action is needed, step 140. When using the compliance data to identify participants likely to produce sufficient, reliable results in a clinical trial, the action taken in step 140 may comprise selecting that participant for a prospective clinical trial or avoiding the participant for future clinical trials based on the production of historically non-compliant data. The action taken in step 140 may alternatively comprise dismissing the participant from an ongoing clinical trial or any other suitable action that would be influenced by the compliance or noncompliance of a participant in a clinical trial.

Decision rules may determine a threshold of compliance or a threshold of noncompliance. The thresholds may be defined empirically and/or algorithmically. In addition, the thresholds used to determine compliance and/or noncompliance to give an indication of performance may be defined by the sponsors of the clinical trial, the vendors, an independent organization or other suitable participant. Optionally, a decision rule may identify a spectrum of noncompliance, from minor noncompliance needing only corrective feedback, to significant noncompliance requiring removal of a participant from the clinical trial. Decision rules may be based on the specific dependent variable used to derive the algorithm or may be based on one or more differing variables.

For example, a subject who, within the first two days of the clinical trial, does not respond to more than 20% of prompted inquiries and either suspends prompting more than once or indicates he/she is napping more than once may be identified as noncompliant, i.e., likely to fail to comply or failing to comply with the research protocol. As another example, subjects who suspend prompting at least twice, and whose total time of such suspension exceeds 2 hours, might be determined to be likely noncompliant, regardless of their overall performance. In another example, administrators who fail to provide proper training to subjects on multiple or a certain number of occasions (determined by the algorithm) may be judged or determined to be noncompliant. A clinical trial site that fails to reach enrollment targets on a given number of occasions might also be determined to be noncompliant, regardless of the overall performance of the site. For purposes of illustration, one sample decision rule may be stated as:

> Display noncompliance remediation message to clinical staff if: [0.32 (ratio of missed random prompts)+0.45 (mean number of minutes spent time delaying assessments per day/100)+0.80 (mean number of hours spent in sleep each night over past 7 days/10)]>1 where if noncompliance is determined by this decision rule, an action, such as sending a specific message to the clinical staff is recommended. For example, in the present example, the message "Subject is not following the protocol as required, resulting in substantial missed assessments. Call subject." may be determined to be the appropriate action.

According to an embodiment of the invention, criteria for identifying a participant as noncompliant with the research protocol need not overlap with criteria developed for determining whether to drop a participant from the clinical trial or exclude data related to or from that participant from the clinical trial results. For example, the decision rule(s) related to dropping a subject from the clinical trial might be based on failed responses to audible prompts rather than on suspension of prompting.

Typically, a decision rule specifies what type of action is required and may provide specific action details. Action types include corrective, affirmative and anti-fraud actions. Action details may include the content of a message to be provided to a subject, clinical staff monitoring staff, or sponsors.

Decision rules may be translated from algorithms that identify patterns of non-compliance data that are harbingers or leading indicators of later, more serious, non-compliance. This would allow early action to be taken based on these indicators. Such decision rules would typically be in the form of contingencies or conditions based on early compliance indicators.

Optionally, translation of algorithms to decision rules may involve human input or additional factors. For example, balancing the impact of a decision rule against the focus of the clinical trial may result in an alteration of the decision rule. For example, if subjects' heart rates are being monitored, frequency of prompting or loudness of reminder alerts may be minimized so as not to artificially raise subject heart rates. Also, clinical staff may alter decision rules based on their assessment of external factors outside of the scope of the quantitative analysis. An example may include providing more alerts to clinical staff instead of directly to subjects to provide more interaction between clinical staff and the subjects.

A decision rule may also be used to predict which participants, in particular which subjects, will fail to complete a clinical trial protocol and therefore will fail to produce useful data. The decision rule may alternatively or also identify participants that have already produced nonusable, inaccurate and/or insufficient data due to noncompliance earlier in the clinical trial or in an earlier clinical trial. Therefore, a decision to rule to drop the participant from the clinical trial, or to work to improve participant performance, can be made at an early time. In addition, a decision to avoid using data from a particular participant, such as a clinical trial site, altogether made be made. By providing those conducting a clinical trial with early feedback regarding participant noncompliance with a research protocol, the present invention improves clinical trial data quality and may potentially save both time and money by either improving the compliance of potentially noncompliant participants or excluding unimprovable noncompliant participant early in a clinical trial or before any resources are wasted on beginning a clinical trial.

The decision rule may determine an action based solely on past noncompliance, without requiring an explicit prediction of future compliance. For example, if an analysis of compliance data indicates that a participant has failed to comply with clinical trial protocol, the decision rule based on the analysis may instruct removal of the participant from an ongoing clinical trial.

According to one embodiment of the invention, the principles used to predict compliance and/or fraud may be applied to data as it comes in from a trial to determine the accuracy and/or compliance of the data with research protocol. The prediction may be made from data other than strict "compliance" data, but may include clinical data in the trial.

The generation of a fraud detection algorithm can take many forms. The psychometric properties of the scale itself could be used to identify potentially fraudulent responses. For example, according to one embodiment of the invention, item response theory uses known properties of individual items within an assessment to estimate the probability that an observed pattern of responses is valid. Therefore, a subject answering yes to the question "My headaches are completely debilitating" has a low probability of also answering yes to the question "My headaches are a minor inconvenience" such that observing this pattern of responses could be indicative of fraud. Inconsistencies with trial data may also indicate the manufacture of data by a clinical trial site or other participant. In another example, a clinical trial having a subject indicating that minimal training or monitoring was provided by clinical trial staff has a low probability of the staff indicating that extensive training and/or monitoring was provided.

According to a further embodiment of the invention, the detection of fraudulent or invalid entries in participant-supplied data may be performed similarly to the methods described herein. For example, the analysis could be based on statistical properties of the responses themselves. Thus, as an example, analysis might indicate that when the standard deviation across subject responses on a particular questionnaire are less than 1.0, fraudulent or invalid completion (whether by the subject or by other trial participants) is highly likely.

The content of subjects' responses could optionally be used as a source of data for the fraud detection algorithms if the responses are invariant or relatively invariant. For example, a subject answering 'yes' to all questions, even when the logical content of the questions would suggest some alternating pattern of appropriate responses may indicate fraud. Fraud from other participants may be similarly detected. For example, the invention may identify the manufacture of data by a clinical trial site, meant to deceive the organizers or sponsors of the clinical regarding the number of subjects participating in the clinical trial.

Analysis of fraud could also be based on particular combinations of responses. Thus, subjects who answered that they took pain medication five or more times daily, but who elsewhere indicated either that pain severity was 4, on a scale of 1 to 10, or that pain frequency was 'infrequent' or 'rare', might be flagged as cases likely to be invalid. The response patterns determined to represent potentially fraudulent data need not be logically inconsistent or intuitively invalid. Rather, they are determined to represent potentially fraudulent data based on statistical analysis comparing valid and invalid response profiles. Therefore, questions posed to subjects or other participants in a clinical trial can be tailored to provide opportunities for the subject to contradict, or appear in disagreement with, responses to earlier questions.

In an alternative embodiment, the posing of questions providing opportunities to contradict earlier responses can be interactive. For example, further questions providing opportunities to contradict earlier responses can be posed only if a response to a question appears unusual or if a decision rule indicates earlier indications of potential fraud.

As a further example, the time required for a subject to respond to items could be the foundation for the generation of fraud detection algorithms. For example, evaluability data could be used to estimate the mean length of time subjects take to respond to certain items. In such an example, response latencies less than or more than two standard deviations below those norms could be the basis of identifying the responses as potentially fraudulent. For example, if a question contains 25 words and subjects take an average of 8 seconds to answer the question, responses of less than 1 second could be identified as potentially fraudulent.

Alternatively, the portable electronic device could capture certain ecological data such as temperature or airborne particles, or physiological data, such as concurrent heart rate, suggestive of a particular location, subjective, or physical state, which is inconsistent with the subject's responses, suggesting possible fraud.

In an alternative embodiment of the invention, participants can be included in the clinical trial for the purpose of providing fraudulent data. For example, in a group of 100 subjects, 20 subjects may be asked to provide fraudulent data. By having such fraudulent data among data provided by the subjects, the quantitative analysis of the present invention can be used to ensure the resulting algorithms and decision rules detect the known fraudulent entries. In the event other subjects are also fraudulently recording data without the knowledge of the clinical staff, the algorithms and decision rules will likely also detect such unknown "spontaneous" fraudulent activity.

Each of the above variations for detection of fraud can be used according to various embodiment of the present invention individually, sequentially or in combination.

According to a preferred embodiment of the invention, the system of the invention for automated processing of data collected via a portable electronic device is provided. In this embodiment, the portable electronic device or system is designed to prompt a participant for information and/or collect information as recorded by the participant without prompting. Preferably, each subject in the clinical trial is provided with a portable electronic device. The portable electronic device is preferably used to collect compliance-relevant variables, such as the number of data entry episodes, missed data entry occasions (e.g., instances where the portable electronic device prompts for data, but the subject fails to respond). A database of these variables is preferably processed according to the decision rules to guide the actions of the portable electronic device as described in detail in the copending patent application titled "System for Clinical Trial Subject Compliance", Attorney Docket No. IVQ-002.

The portable electronic device for each subject is also preferably adapted to communicate with another computer to allow the clinical staff to consolidate the data from all subjects in the clinical trial into one location for review or processing. Preferably, the portable electronic device will also be adapted to communicate with at least one other computer via a wireless connection or via a wired connection, including the use of a modem and/or a network, such as a LAN or the Internet. For example, by the use of the Internet or a dial-up modem connection, a subject may submit information from the portable electronic device to the clinical staff from the subject's home.

In another embodiment, a portable electronic device or a computer is adapted to communicate with clinical trial equipment used for measuring, monitoring, controlling or recording data or a process of the clinical trial. Examples of such processes include administration of medication or monitoring of heart rates. The portable electronic device or a computer preferably automatically records desired data for incorporation in the clinical trial data or compliance data.

In another embodiment of the invention, a paper form, such as a case report form, can be used by the subject or other participant to record data. The data can then be entered into a database by the use of a portable electronic device or other computer at an appropriate time. Examples of case report forms include hand-written forms and forms that allow for machine readable marks to be made, enabling automated scanning of the case report forms during entry of the data into a computer.

In an alternative embodiment of the present invention, the methods of the present invention may be incorporated in instructions recorded on a medium suitable for use in an electronic device, such as a computer, computer network server or a portable electronic device. The medium can include, for example, a hard disk, RAM medium, diskette, CD-ROM or other optical or magnetic storage medium. The instructions can optionally be stored on a server that can be remote from the subject or clinical staff member.

According to an embodiment of the invention, the server can provide data to be displayed. Data may be displayed at the server itself or be transmitted to another location, such as via hardwired or wireless access to the server, including a LAN or the Internet. The data can be processed to provide a graphical display to interested parties. Examples of those who may be interested in viewing the graphical representation of the compliance data include a site coordinator (who may be interacting with the subject), a clinical research organization (who may be responsible for study execution across a number of research locations), other agencies interested in the collection of the data, or the sponsor of the research.

According to another embodiment of the invention, the server can provide ongoing aggregation of data across participants to speed the time required to combine, clean, and make available final data.

In another embodiment of the invention, a compliance database, such as an Excel® database, may be compiled using compliance data collected from one or more clinical trials. The compliance database may be used to predict compliance of any clinical trial participant in a future clinical trial, predict continued compliance in an ongoing clinical trial and/or identify noncompliance in a clinical trial. The compliance database may be used by sponsors of a clinical trial to select participants that will most likely yield accurate, useful results without wasting resources.

The compliance database may contain many different metrics on the participant performance, as described above. For example, for particular clinical trial sites, the compliance data in the database may list the historic ability of each site to reach enrollment targets, how compliant each sites was in previous clinical trials with respect to training, subject compliance, and regular trial monitoring and other data indicative of compliance and therefore overall performance.

In this manner, a sponsor of a clinical trial may identify highly qualified participants, such as clinical trial sites that historically produce adequate, accurate and reliable data, for conducting a clinical trial, and avoid wasting resources on participants that will not tend to produce usable results, such as non-performing clinical sites.

For example, the performance of targeted clinical sites in previous clinical trials may be tracked according to an embodiment of the invention in several different ways. The resulting database allows for statistical analysis and identification only those clinical sites that have been able to meet their enrollment targets and excel in compliance with research protocols in other clinical trials. Selected clinical sites may then be ranked in a given therapeutic category to identify the premier clinical sites that are most likely to succeed in a proposed clinical trial.

These examples are meant to be illustrative and not limiting. The present invention has been described by way of example, and modifications and variations of the exemplary embodiments will suggest themselves to skilled artisans in this field without departing from the spirit of the invention. Features and characteristics of the above-described embodiments may be used in combination. The preferred embodiments are merely illustrative and should not be considered restrictive in any way. The scope of the invention is to be measured by the appended claims, rather than the preceding description, and all variations and equivalents that fall within the range of the claims are intended to be embraced therein.

What is claimed is:

1. A computer implemented method of determining noncompliance of a participant in a clinical trial, comprising the steps of:
providing historical participant compliance data;
generating at least one algorithm for determining participant noncompliance by quantitative analysis of the historical participant compliance data;
applying the at least one algorithm to determine participant compliance; and
outputting notice of noncompliance.

2. The method of claim 1, further comprising the step of translating the at least one algorithm into at least one decision rule for use with a clinical trial.

3. The method of claim 2, further comprising the step of selecting the participant for a prospective clinical trial based on the at least one decision rule.

4. The method of claim 3, further comprising the step of dropping the participant from the clinical trial based on the at least one decision rule when the algorithm identifies the participant as noncompliant.

5. The method of claim 1, wherein the participant is a particular clinical trial site, and the historical participant compliance data includes enrollment levels in previous clinical trials conducted by the particular clinical trial site.

6. The method of claim 1, wherein the participant is a particular clinical trial site, and the historical participant compliance data includes achievement of target enrollment levels in previous clinical trials conducted by the particular clinical trial site.

7. The method of claim 1, wherein the participant is a particular clinical trial site, and the historical participant compliance data includes data regarding the compliance of a clinical trial site with research protocols in previous clinical trials.

8. The method of claim 7, wherein the data regarding compliance of a clinical trial site with research protocols relates to at least one of: training provided to subjects, monitoring of subjects during a clinical trial and compliance of subjects participating in clinical trials conducted by the clinical trial site.

9. The method of claim 1, wherein the historical participant compliance data includes compliance data for subjects in clinical trials involving the participant.

10. The method of claim 1, further comprising the step of storing the historical participant compliance data in a database.

11. The method of claim 10, wherein the database stores historical participant compliance data for a plurality of participants in a clinical trial.

12. The method of claim 11, wherein at least one algorithm for determining participant noncompliance by quantitative analysis of the historical participant compliance data is generated for each participant.

13. The method of claim 1, wherein the historical participant compliance data is collected at an earlier point in time during the clinical trial.

14. The method of claim 1, wherein the historical participant compliance data is collected during a previous clinical trial.

15. The method of claim 1, wherein the participant is one of: a medical professional conducting the clinical trial, a subject in the clinical trial, an administrator of the clinical trial, an investigator, a study coordinator, a data collector, a clinical trial monitor, a clinical trial site, a sponsoring pharmaceutical company and a contract research organizations that provides training for clinical trial sites and personnel.

16. A computer implemented method of identifying a suitable clinical trial site for conducting a clinical trial, comprising the steps of:
providing a database storing historical compliance data for a plurality of clinical trial sites;
performing a statistical analysis of the historical compliance data for each clinical trial site to predict compliance in a future clinical trial; and
selecting a clinical trial site that is predicted to comply with research protocols.

17. The method of claim 16, wherein the database ranks clinical trial sites according to a likelihood of compliance in a future clinical trial.

18. The method of claim 17, wherein the database ranks clinical trial sites in a specific therapeutic category.

19. The method of claim 16, wherein the historical compliance data includes enrollment levels for prior clinical trials.

20. The method of claim 16, wherein the historical compliance data includes a ratio between a number of clinical trials conducted and a number of clinical trials in which target enrollment levels were achieved.

21. The method of claim 16, wherein the historical compliance data includes compliance of subjects participating in previous clinical trials conducted by each clinical trial site with research protocols.

22. The method of claim 16, wherein the historical compliance data relates to at least one of: training provided to subjects by the clinical trial site and monitoring of subjects during a clinical trial.

23. A computer implemented method of predicting success of a clinical trial involving a selected clinical trial participant, comprising the steps of:
providing historical compliance data from a clinical trial involving the clinical trial participant;
performing a quantitative analysis of the data to identify whether the participant is likely to produce data in compliance with research protocol in the future; and
identifying whether the participant is likely to produce data in compliance with research protocols in the future.

24. The method of claim 23, wherein the historical compliance data is collected in a previous clinical trial from the clinical trial for which success is predicted.

25. The method of claim 23, wherein the historical compliance data is collected at an earlier point in the clinical trial for which success is predicted.

26. The method of claim 23, wherein the statistical analysis predicts compliance in a future clinical trial.

27. The method of claim 23, further comprising the step of selecting the participant for a clinical trial based on the quantitative analysis.

28. The method of claim 23, further comprising the step of dropping the participant from the clinical trial for which success is predicted based on the quantitative analysis.

29. The method of claim 23, wherein the research protocol includes performance goals of a clinical trial.

30. The method of claim 11, further comprising the step of ranking the plurality of participants based on a likelihood of each participant complying with protocols for a future clinical trail, determined by an algorithm associated with each participant.

* * * * *